(12) United States Patent
Lee

(10) Patent No.: US 9,364,553 B2
(45) Date of Patent: Jun. 14, 2016

(54) SYNERGISTIC BIOMOLECULE-POLYMER CONJUGATES

(71) Applicant: PEG Biosciences, Inc., Monmouth Junction, NJ (US)

(72) Inventor: Chyi Lee, Princeton Junction, NJ (US)

(73) Assignee: PEG Biosciences, Inc., Monmouth Junction, NJ (US)

( * ) Notice: Subject to any disclaimer, the term of this patent is extended or adjusted under 35 U.S.C. 154(b) by 0 days.

(21) Appl. No.: 14/444,555

(22) Filed: Jul. 28, 2014

(65) Prior Publication Data

US 2014/0335051 A1    Nov. 13, 2014

Related U.S. Application Data

(63) Continuation of application No. 13/817,702, filed as application No. PCT/US2011/048468 on Aug. 19, 2011, now abandoned, application No. 14/444,555, which is a continuation of application No. 12/302,238, filed as application No. PCT/US2007/069697 on May 24, 2007, now abandoned.

(60) Provisional application No. 61/375,164, filed on Aug. 19, 2010, provisional application No. 60/808,175, filed on May 24, 2006.

(51) Int. Cl.
| | |
|---|---|
| *A61K 47/30* | (2006.01) |
| *A61K 47/48* | (2006.01) |
| *C07K 1/107* | (2006.01) |
| *C07K 17/06* | (2006.01) |
| *C08G 65/333* | (2006.01) |
| *C08G 65/332* | (2006.01) |

(52) U.S. Cl.
CPC ............ *A61K 47/48215* (2013.01); *A61K 47/48* (2013.01); *A61K 47/48169* (2013.01); *C07K 1/1077* (2013.01); *C07K 17/06* (2013.01); *C08G 65/332* (2013.01); *C08G 65/33344* (2013.01); *C08G 65/33396* (2013.01); *C08L 2203/02* (2013.01)

(58) Field of Classification Search
None
See application file for complete search history.

(56) References Cited

U.S. PATENT DOCUMENTS

2008/0058246 A1*   3/2008   Bhaskaran et al. ............... 514/2

FOREIGN PATENT DOCUMENTS

| EP | 0732109 | * | 2/1996 | ............ A61L 27/00 |
| WO | WO 2007/140282 | * | 12/2007 | ............ A61K 39/00 |

OTHER PUBLICATIONS

Web MD screenshot, accessed on Apr. 16, 2015, available at www.webmd.com/drugs/condition-850-Blood%20Clotting% 20Disorder% 20from%20Clotting%20Factor%20IX.aspx?diseaseid=850&diseasename=Blood+Clotting+Disorder+from+Clotting+Factor+IX.*
Bailon et al., Bioconjugate Chem. (2001) 12, 195-202.*

* cited by examiner

*Primary Examiner* — Marcela M Cordero Garcia
*Assistant Examiner* — Catherine Mader
(74) *Attorney, Agent, or Firm* — Fox Rothschild LLP; Gerard P. Norton; Robert N. Henrie, II

(57) ABSTRACT

The synergistic biomolecule-polymer conjugates are the long-acting, in vivo controlled continuous-release and hybrid synergy systems of biomolecules that provide increased biological activities and enhanced pharmacological properties for achieving greater therapeutic efficacies.

25 Claims, No Drawings

SYNERGISTIC BIOMOLECULE-POLYMER CONJUGATES

CROSS-REFERENCE TO RELATED APPLICATIONS

This application is a continuation of U.S. patent application Ser. No. 13/817,702, filed Mar. 19, 2013, which is a U.S. National Phase application of International Application No. PCT/US11/048468, filed Aug. 19, 2011, which claims priority to U.S. Provisional Patent Application No. 61/375,164, filed Aug. 19, 2010, the disclosures of which are hereby incorporated by reference in their entirety. This application is also a continuation of U.S. patent application Ser. No. 12/302,238, filed Nov. 24, 2008, which is a U.S. National Phase application of International Application No. PCT/US07/069697, filed May 24, 2007, which claims priority to U.S. Provisional Patent Application No. 60/808,175, filed May 24, 2006, the disclosures of which are hereby incorporated by reference in their entirety.

FIELD OF THE INVENTION

The present invention relates to the novel synergistic biomolecule-polymer conjugates produced from the attachment of the permanent-cleavable-linkages or all-cleavable-linkages polymers to biologically active molecules to provide synergistically enhanced biological activities in vivo and improved pharmacokinetic (PK) and pharmacodynamic (PD) properties of delivered biomolecules for achieving optimum therapeutic efficacies. The synergistic biomolecule-polymer conjugates integrate the advantages of PK and PD properties of large and small biomolecule-polymer conjugates in vivo. The present invention further relates to the novel synergistic Interferon-α-polymer (Synergy-IFN-α-polymer) conjugates, which are the in vivo enzyme-controlled, continuous-release and hybrid synergy systems of interferon that provide the increased biological activity and enhanced pharmacological properties for achieving greater interferon-α related therapies.

BACKGROUND OF THE INVENTION

Coupling of polyethylene glycol (PEG) to biologically active molecules termed "Pegylation" are used in the delivery biologically active molecules usually proteins and small molecules. At least one advantage of this process is modifying the pharmacokinetic (PK) and pharmacodynamic (PD) properties of the biologically active molecules and improving therapeutic effectiveness of the biologically active molecules. Pegylation increases the size and molecular weight of proteins and small molecules resulting in the extension of their half-life in plasma. In general, Pegylation may alter the physicochemical properties of the proteins and therapeutic molecules resulting in decreased bioactivity of the parent proteins and organic therapeutic molecules. It is therefore desirable to optimize the PK and PD properties of PEG-protein conjugates for achieving their maximum therapeutic efficacies.

Covalently attaching PEG to biologically active molecules in the prior art, including linear and branched PEG polymers, has been achieved. In vast majority of cases amino groups of the biologically active molecules are utilized as the sites of attachment. US Patent Application 20030190304 to Thompson et al. describes Pegylation reagents. U.S. Pat. No. 7,030,278 to Harris et al. describes certain PEG derivatives with proximal reactive groups. Certain non-antigenic branched polymer conjugates are described in U.S. Pat. No. 5,643,575 to Martinez et al. Certain multi-armed PEG polymers are described in the US Patent Application 20050033058 to Huang et al. Certain active carbonates for modification of polypeptides are disclosed in U.S. Pat. No. 5,122,614 to Zalipsky. Interferon polymer conjugates utilizing stable (permanent) linear PEG polymers for conjugation are described in U.S. Pat. No. 5,711,944 to Gilbert et al. Interferon polymer conjugates utilizing stable branched PEG polymers for conjugation are described in U.S. Pat. No. 5,932,462 to Milton et al.

Protein drugs of molecular mass lower than 50,000 Daltons are in general short-lived species in vivo, having a circulatory half-life of about 5-20 min. Clearance of proteins occurs through several mechanisms, including glomerular infiltration in the kidney, receptor-mediated endocytosis, and degradation by peripheral tissues, and proteolysis at the tissue surfaces or by serum proteases. Considering also that protein drugs are not absorbed orally, prolonged maintenance of therapeutically active drugs in circulation is a desirable feature of primary clinical importance. This condition, however, is rarely achieved after a single administration of low molecular weight peptides and protein drugs. At least one strategy to achieve such goals described in the art is pegylating such biomolecules. However, the drawback in prior art Pegylation methodologies is the loss of biological activity of the proteins that are pegylated by conventional permanent branched or linear PEG compounds. Such loss of biological activity is due to the steric hindrance created by the large PEG polymers that are being attached to the biologically active protein of interest. For example, the pegylated interferons, such as Pegasys using permanent branched PEG or Peg-Intron using linear PEG for Interferon-α conjugation only retain 7 and 28% specific antiviral activity of the unmodified Interferon α-2a and Interferon α-2b, respectively. For many therapeutic proteins, a significant loss in biological activity can result in a poor PK-PD profile which often limits the therapeutic application of Pegylation. The numbers and sizes of PEG have significant impacts on proteins' biological activity, pharmacokinetic and pharmacodynamic properties.

Another question that remains unanswered in the art is whether prolonging half-lives of short-lived proteins sequentially in vivo, by allowing controlled degradation of the polymeric linkages would prolong therapeutic drug availability in vivo, thus improving clinical outcome. Given the above, it is desirable to have biomolecule-polymer conjugates that overcome these deficiencies. The instant invention remedies these shortcomings in the prior art.

SUMMARY OF THE INVENTION

At least one aspect of the present invention provides the novel synergistic biomolecule-polymer conjugates (Types Ia, Ib, IIa and IIb), which are biomolecules covalently attached to branched or linear polymers via cleavable-linkages. The synergistic biomolecule-polymer conjugates, as used in this application, are the long-acting, controlled continuous release and/or hybrid synergy systems that when administered in vivo provide enhanced biological activities and improved pharmacological properties of the biomolecules as compared to its counterpart unconjugated biomolecules or in the alternative as compared to biomolecules which are conjugated to the same polymers via non-cleavable linkages.

At least one aspect of the present invention is directed to synergistic biomolecule-polymer conjugates having the formulas I or II:

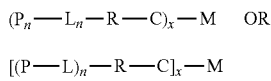

Formula I

[(P—L)$_n$—R—C]$_x$—M       Formula II wherein M is a biologically active molecule; wherein x is the number of cleavable-linkages polymers coupled to a biomolecule and x≥1; wherein n is n≥2; wherein P is polymer or polymer lipid; wherein Pn are multiple polymeric arms or pieces that their types and sizes may be the same or different; wherein L is a functional linkage moiety containing at least one cleavable linkage and at least one permanent linkage; or Ln are releasable linkages; and wherein R is a non-cleavable spacer connected between polymer and biomolecule; C is a coupling group capable of attaching to a biomolecule.

The synergistic biomolecule-polymer conjugates of the present invention include at least four types of conjugates, namely Types Ia, Ib, IIa and IIb Biomolecule-polymer conjugates. Type Ia synergistic biomolecule-polymer conjugates contain permanent-cleavable-linkages between branched polymers. Type Ib synergistic biomolecule-polymer conjugates contain all-cleavable-linkages among branched polymers. Type IIa synergistic biomolecule-polymer conjugates contain permanent-cleavable-linkages between linear polymers. Type IIb synergistic biomolecule-polymer conjugate contain all-cleavable-linkages between linear polymers.

The presently disclosed novel permanent-cleavable-linkages or all-cleavable-linkages employed in the instant synergistic bioconjugates can therefore contain either branched or linear polymers within the construct. Type I is the branched cleavable-linkages polymers and Type II is the linear cleavable-linkages polymers. The cleavable linkage as used herein include in vivo cleavable, blood plasma cleavable, enzymes cleavable or pH-dependent hydrolysable linkages.

Type I branched cleavable-linkages polymers include the permanent-cleavable-linkages branched polymers (Type Ia) and the all-cleavable-linkages branched polymers (Type Ib). Type II linear cleavable-linkages polymers include the permanent-cleavable-linkages linear polymers (Type IIa) and the all-cleavable-linkages linear polymers (Type IIb). A permanent-cleavable-linkages branched polymer as used herein contains both cleavable and permanent linkages, wherein Ln linkages are cleavable-permanent-mixed-linkages. An all-cleavable-linkage branched polymer contains only cleavable-linkages, wherein Ln linkages are only cleavable linkages.

In blood plasma and/or in vivo, a synergistic bioconjugate of permanent-cleavable-linkages polymer Type Ia or Type IIa is cleaved and converted into smaller moieties including smaller sized bioactive polymer-spacer-biomolecule fragments and polymers via enzymatic reactions.

In blood plasma and/or in vivo, a synergistic bioconjugate of all-cleavable-linkages polymer Type Ib or Type IIb is degraded to smaller moieties including smaller sized biomolecule-spacer fragments and polymers via enzymatic reactions.

At least one advantage of the present invention is that the bioconjugates of the present invention are degraded into multiple bioactive fragments that not only possess suitable steric characteristics for exerting its biological activity, but also are cleaved into moieties that are readily excreted or cleared from the body. In contrast, the conventional protein conjugates of prior art are branched polymers that are linked via permanent linkages, linking the polymeric arms, so that such polymers stay stable in blood plasma and as the result exacerbate systemic toxicity and undesirable tissue accumulation of non-degradable polymeric moieties.

Another embodiment of the present invention is contemplated in the formula III below, wherein n=2 within the framework of Formula II. Accordingly, the synergistic biomolecule-branched polymer conjugate is represented by the formula III having the structure:

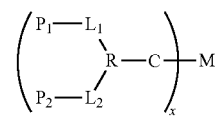

Formula III

Accordingly, for Type Ia permanent-cleavable-linkages (mixed-permanent-cleavable linkages) branched polymers, $L_1$ is a permanent linkage and $L_2$ is a cleavable linkage.

For Type Ib all-cleavable-linkages branched polymers, both $L_1$ and $L_2$ are the cleavable linkages.

At least another embodiment according to Formula I is, when n=2, the synergistic biomolecule-linear polymer conjugate is represented by the structure having the Formula IV:

($P_2$-$L_2$-$P_1$-$L_1$-R—C)$_x$-M       Formula IV

Accordingly, for Type IIa permanent-cleavable-linkages linear polymers, wherein $L_1$ is a permanent linkage and wherein $L_2$ is a cleavable linkage.

For Type IIb all-cleavable-linkages linear polymers, both $L_1$ and $L_2$ are the cleavable linkages.

The novel synergistic biomolecule-polymer conjugates (Synergy-biopolymers), are the in vivo controlled, continuous-release and hybrid synergy systems of biomolecule-polymer conjugates. The synergistic biomolecule-polymer conjugates are slowly degraded to smaller sizes but more active biomolecule-polymer fragment (or biomolecule-spacer) conjugates via in vivo enzymatic reactions. The enhanced combined biological activities generated from the synergistic biomolecule-polymer conjugate and the released biomolecule-polymer fragment (or biomolecule-spacers) conjugates provide drug synergism for the biomolecule related therapies. The synergistic biomolecule-polymer conjugates of the invention are the unique biomolecule delivery systems that further provide enhanced pharmacokinetic (PK) and pharmacodynamic (PD) properties of biomolecules for achieving optimum therapeutic efficacies.

One of the major advantages of the invention is the ability of synergistic biomolecule-polymer conjugates to generate hybrid synergy biological activities in vivo through the combined bioactivities from the large biomolecule-polymer and the released smaller biomolecule-polymer conjugates. Unlike the conventional branched polymer-biomolecule conjugate contains only permanent polymeric linkages so that the conjugate does not release its polymeric arms in plasma and thus, has a fixed biological activity.

At least another advantage of the invention is that the unique synergistic biomolecule-polymer conjugates that integrate the advantages of large biomolecule-polymer conjugates' PK properties and small biomolecule-polymer (or biomolecule-spacer) conjugates' PD properties to maximize the overall PK-PD profile of the biomolecule-polymer conjugates for its beneficial therapeutic effects.

Additional advantage is the synergistic biomolecule-polymer conjugate provides linkage cleavage mechanism to reduce the size of biomolecule-polymer by releasing bulky polymers in vivo and thus, reducing the toxicity. The synergistic biomolecule-polymer conjugate provides advantages over conventional protein-polymer for prophylactic therapies, such as factors VII, VIII, IX for hemophilia, etc.

The novel synergistic biomolecule-polymer conjugate provides in vivo hybrid synergy biological activity and pharmacological properties for achieving increased, consistent and sustained biomolecular drug's activity in plasma. Thus, the synergistic biomolecule-polymer conjugates offer substantial benefits over the conventional polymer conjugates.

Another aspect of the invention provides for a method of preparing synergistic biomolecule-polymer conjugates. In this aspect of the invention, methods of synthesizing the above mentioned permanent-cleavable-linkages and all-cleavable-linkages polymers for the preparation of the synergistic biomolecule conjugates are described. In another embodiment methods for pro synthesizing linker polymers are also described.

An additional aspect of invention relates to the attachment of permanent-cleavable-linkages branched polymers to interferon-α to produce synergistic interferon-α polymer conjugates (Synergy-IFN-α polymer conjugates). The novel Synergy-IFN-α polymer conjugates release partial polymeric arms in vivo via enzymatic reactions and convert into smaller but more active Interferon-α polymer conjugates, resulting in combined increased of the interferon bioactivity and combined enhanced-pharmacokinetic and pharmacodynamic properties.

Unlike the conventional interferon-α-polymer conjugates, the novel synergistic interferon-α-polymer (Synergy-IFN-α-polymer) conjugates of the invention are the in vivo controlled, continuous-release and hybrid synergy systems of interferon-α that deliver the optimum pharmacological properties combined from large and small interferon-α-polymer conjugates in vivo. The Synergy-IFN-α-polymer conjugates integrate advantages of the large interferon-α-polymer having longer $T_{1/2}$ and the small interferon-α-polymers having higher bioactivity for achieving increased, consistent and sustained antiviral activity in plasma. Clinically, the Synergy-IFN-α-polymer may result in attaining greater sustained virological response with subsequent reduction in dose, dosing frequency, or even disease treatment period for the interferon-α related therapies. Therefore the Synergy-IFN-α-polymer conjugates may offer significant clinical advantages over the conventional pegylated interferon-α conjugates.

DETAILED DESCRIPTION OF THE INVENTION

The invention of Probiomolecule-PEG conjugation was mentioned in U.S. patent application Ser. No. 12/302,238, the content thereof is incorporated herein by reference in its entirety. The permanent-cleavable-linkages (also refer herein as mixed-permanent-cleavable linkages) or all-cleavable-linkages branched or linear polymers include those linkages described in the same patent application. At least one aspect of the present invention is the unexpected increase in the in vivo efficacy offered by the claimed linkers achieved by enhancing the PK and PD properties for the disclosed. One shortcoming in the art for delivery of biomolecules is that the peptide and the protein compounds have a very short plasma half life time. Such short plasma half life times are commonly due to fast renal clearance as well as to enzymatic degradation occurring during systemic circulation.

It is unexpected to offer strategies to prolong plasma half life time and at the same time improve the effectiveness of therapeutic protein in vivo. Such unexpected observation is due to achieving a critical balance obtained between the PK and PD of the claimed compounds and constructs.

At least one aspect of the present invention is the instantly disclosed constructs ability to provide a maximize PK-PD profile. The present invention discloses continuous and delayed cleaving of the protein-PEG linkages coupled with a prolong plasma half-life characteristics offered by the permanent protein-PEG linkage alter the in vivo efficacy of protein drugs so that a decrease in potency caused by reduced binding affinity is compensated for by an increase in the overall systemic exposure caused by the prolonged plasma circulating time. Accordingly, the present invention discloses an overall enhancement of therapeutic benefit of the biomolecule of interest by harmonizing the PK-PD profile of the disclosed conjugates. This outcome provides an unexpected therapeutic benefit never previously realized in such unpredictable art.

Unlike the conventional Pegylation methodologies described in the art that utilize the branched permanent-linkages (PEG2, UPEG, Y-shaped) or linear permanent-linkages PEG linkers (SC-PEG, etc.) for proteins conjugation, the present invention provides four types of synergistic biomolecule-polymer conjugates, that contain branched or linear polymer linkers attached to biologically active molecules via permanent-cleavable-linkages or all-cleavable-linkages. These conjugates include biomolecules connected with the permanent-cleavable-linkages branched polymer (Type Ia) and all-cleavable-linkages branched polymer (Type Ib) and permanent-cleavable-linkages linear polymer (Type IIa) and all-cleavable-linkages linear polymer (IIb).

The present invention provides the synergistic biomolecule-polymer conjugates, which are biomolecules covalently attached to the cleavable-linkages polymers (Types Ia, Ib, IIa and IIb). The synergistic biomolecule-polymer conjugates are the long-acting, continuous release and hybrid synergy systems that in vivo provide enhanced biological activities and improved pharmacological properties for the delivered therapeutic agents.

Those of ordinary skill in the art of organic chemistry and prodrug science would appreciate that permanent (or stable) linkages are covalent and non-degradable covalent bonds in vivo. In other words, these are non-hydrolyzable linkages that do not readily cleave in blood plasma. On the other hand, releasable (or cleavable) linkages are regarded as hydrolyzable or degradable linkages in blood plasma.

As used herein, a cleavable-linkage in the permanent-cleavable-linkages or all-cleavable-linkages refer to a bond linkage that when in vivo, it is cleaved. Such linkages include those that are blood plasma cleavable, enzyme degradable, pH-induced hydrolyzable, pH-induced self-cleavable, in vivo substance induced cleavable, biochemical reaction induced cleavable, or chemically cleavable.

The novel synergistic biomolecule-polymer conjugates produced from the attachment of the cleavable-linkages polymer linkers can contain at least one cleavable linkage in this invention correspond to the following formulas I and II as described above:

$$(P_n\text{-}L_n\text{-}R\text{—}C)_x\text{-}M \text{ OR } [(P\text{-}L)_n\text{-}R\text{—}C]_x\text{-}M$$

Wherein M is a biologically active molecule; wherein x is and is a number x≥1; Wherein n is a number defined as n≥2; wherein P is polymer or polymer-lipid; wherein Pn are multiple polymeric arms or pieces that their types and sizes may be the same or different; wherein L is a functional linkage connected between a polymer and a spacer or a linkage between polymers and wherein L is a functional linkage moiety comprising at least one cleavable linkage and at least one permanent linkage; or Ln are all cleavable linkages; wherein R is a non-cleavable compound or spacer moiety connected between polymer and biomolecule; and R having at least two functional groups for linking to P for Type I branched polymer; wherein C is a coupling group capable of attaching to a biomolecule. At least another embodiment within the present invention requires the formulas I and II above, contain linkage moiety to have at least one permanent linkage and at least one releasable linkage.

The polymers used for synergistic biomolecule-polymer conjugates are preferably water-soluble. A non-limiting list of such polymers include polyalkylene oxide homopolymers such as polyethylene glycol (PEG) or polypropylene glycols, poly(vinyl alcohol), poly(oxyethylated glycerol), poly(oxyethylated sorbitol), poly(oxyethylated glucose), poly(oxazoline), poly(acryloylmorpholine), poly(vinylpyrrolidone), polyoxyethylenated polyols, copolymers, block copolymers, terpolymers, and mixtures thereof. The polyalkylene oxides containing alkyl terminals, such as monomethoxy polyethylene glycols (mPEG) are also included.

Besides polyalkylene oxide polymers, other polymers such as polyethylene imine, dextran, PEG-lipids, polymer lipids, polyacrylamides, polyvinyl alcohols, carbohydrate polymers and a similar kind of polymers can be used.

Polyethylene glycol (PEG) and monomethoxy polyethylene glycols (mPEG) are the particularly preferred polymer. Molecular weight of PEG is in the range from about 50 to about 40,000. PEG having molecular weight ranging from 5,000 to 40,000 is particularly useful for protein conjugation.

The lipid moieties connected to polymer include, but are not limited to, fatty acyls, glycerolipids, glycerophospholipids, sphingolipids, saccharolipids and polyketides and sterol lipids and prenol lipids, phospholipids and ceramids The particularly preferred polymer-lipids are PEG-phospholipids and PEG-ceramides. The permanent-cleavable-linkages or all-cleavable-linkages polymer-lipid can be used for the formation of liposome or nanoparticle with biologically active molecules. A synergistic biomolecule-polymer conjugate can be a liposome or a nanoparticle.

The spacer R include, but is not limited to chemicals, drugs, peptides, amino acids, nonprotein amino acids, nonprotein amino acid derivatives, amino acid derivatives, DNA fragment or RNA fragment, or mixed thereof. In addition, the amino acids of Type I branched polymers is selected from the group consisting of lysine, serine, threonine, cysteine, tyrosine, histidine, arginine, glutamic acid or aspartic acid. Furthermore, the nonprotein amino acid of Type I branched polymers is selected from the group consisting of homocysteine, homoserine or ornithine. The spacer R can be an amino acid or non-protein amino acid further connected with other chemicals.

As used herein, a cleavable linkage is in vivo cleavable, blood plasma cleavable, enzymes degradable, pH-dependent hydrolyzable, pH induced self-cleavable, physiologically cleavable, in vivo substance induced cleavable, biochemical reaction induced cleavable, or chemically cleavable. The cleavable linkages include, but are not limited to, the group of carboxylic ester, carbonate, sulfonic ester, phosphoric ester, acylimidazo, carbamate-imidazo, and disulfide.

Enzymes involved in cleaving linkages in vivo and/or plasma include hydrolytic enzymes, reductive enzymes and oxidative enzymes. The enzymes include, but not limited to, esterases, phosphatases, sulfatases, proteases, disulfide reductases, keto reductases, dehydrogenases, peroxidases and amine oxidases, esterases, phosphatases and sulfatases are particularly preferred enzymes. The carboxylic ester and carbonate linkages are cleaved by esterase enzymes. Thus, the term enzyme degradable herein include linkages that are all degraded or cleaved by said enzymes. The permanent linkage is non-cleavable in blood plasma. The permanent linkages include, but not limited to, the group of amide, carbamate, carbamide, imide, amine, urea, ether, urethane, sulfide, thiourea, thiocarbamate, thiocarbamide, and dithiocarbamate.

The C coupling group contains electrophilic or nucleophilic groups. The electrophilic group groups include, but are not limited to, N-hydroxysuccinimide (NHS) ester, p-nitrophenyl ester, succinimidyl carbonate, p-nitrophenyl carbonate, succinimidyl urethane, isocyanate, isothiocyanate, acyl azide, sulfonyl chloride, aldehyde, carbonate, imidioester, anhydride, mixed anhydride, maleimide, haloacetyl, alkyl halide derivatives, aziridine, acryloyl derivatives arylating agents and thio-disulfide exchange reagents. The nucleophilic functional groups include, but not limited to, amino, hydroxyl, hydrazide, carbazate, acyl hydrazide, semicarbamate and hydrazine.

When x is x≥1, the number of cleavable-linkages polymers attached to a biologically active molecule via the C coupling groups can vary from one single to multiple cleavable-linkages polymers. A synergistic biomolecule-polymer conjugate of the invention can be a mixture of biomolecule containing various numbers of cleavable-linkages polymers. The mixture can be a combination of conjugates containing different x numbers. For example, a mixture is consisted of certain percentages of biomolecule-monopolymer (x=1) and biomolecule-dipolymer (x=2). Also, a synergistic biomolecule-polymer conjugate can be further purified for desired numbers of cleavable-linkages polymers by methods such as ionic chromatography, gel filtration chromatography, affinity chromatography, reverse phase chromatography, ultrafiltration, diafiltration, dialysis, centrifugation, etc.

The M Biologically active molecules (biomolecules) attached to permanent-cleavable-linkages or all-cleavable-linkages polymers include, but not limited to, protein, glycoprotein, oligopeptide, polypeptide, enzyme, cytokine, hormone, antibody, monoclonal antibody, antibody fragment, single-chain antibody, monoclonal antibody, nucleic acid, DNA, RNA, RNAi, siRNA, oligonucleotide, oligosaccharide, polysaccharide, hormone, neurotransmitter, carbohydrate, sugar, disaccharide, lipid, phospholipid, glycolipid, sterol, amino acid, nucleotide, cell permeable peptide, small molecular drugs, etc.

Potential biomolecules for the applications of PEG permanent-cleavable-linkages and all-cleavable-linkages for synergistic biomolecule-PEG include, but not limited to, cytokines, epoetin alfa, granulocyte colony-stimulating factor (G-CSF), etanercept, interferons, interferon α-2a, interferon α-2b, interferon alfacon-1, interferon β-1a, interferon β-1b, interferon γ-1b, interleukins, TNF-α, insulin, urokinase, streptokinase, uricase, superoxide dismutase, asparaginase, arginine deaminase, glucocerebrosidase, galacosidase, retelapse, rasburicase, laronidase, oprelvekin, dornase α, collagenase, anistreplase, agalsidase, growth factors, hemoglobin, blood clotting factors, blood clotting factors VII, VIIa, VIII, and IX, etc.

As described above, the present invention includes four types of synergistic biomolecule-polymer conjugates (Types Ia, Ib, IIa and IIb) attached with branched and linear cleavable-linkages polymers. A Type Ia synergistic biomolecule-polymer conjugate comprises the permanent-cleavable-linkages branched polymers. A Type Ib synergistic biomolecule-polymer conjugate comprises the all-cleavable-linkages branched polymers. A Type IIa synergistic biomolecule-polymer conjugate comprises the permanent-cleavable-linkages linear polymers. A Type IIb synergistic biomolecule-polymer conjugate comprises the all-cleavable-linkages linear polymers.

For example, if n=2, the synergistic conjugates attached with cleavable-linkages branched polymer (Type I) is represented by the Formula III:

Formula III

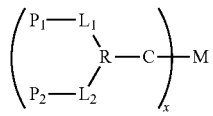

For Type Ia synergistic conjugates attached with permanent-cleavable-linkages branched polymers, wherein $L_1$ is a permanent linkage; wherein $L_2$ is a cleavable linkage.

If x=1, the Type Ia synergistic conjugates is gradually converted to $P_1$-$L_1$-R—C-M and $P_2$ in vivo and/or in plasma via enzymes controlled degradation reactions. This unique synergistic biomolecule-polymer provides combined dual active biomolecule-polymer conjugates in vivo, including the large size synergistic biomolecule-polymer and the small fragmented biomolecule-polymer conjugates formed as the result of the enzymatic degradation.

For Type Ib synergistic conjugates attached with all-cleavable-linkages branched polymers, both $L_1$ and $L_2$ are the cleavable linkages.

When x=1, the Type Ib synergistic conjugates is gradually converted to R—C-M, $P_1$ and $P_2$ in vivo and/or in plasma via enzymes controlled reactions. This synergistic biomolecule-polymer provides combined biomolecule-polymer conjugates in vivo, including the large size synergistic biomolecule-polymer and the small biomolecule-spacer conjugates.

In general, the large molecular size of biomolecule-polymer conjugate has longer blood plasma circulating time but decreased bioactivity. The small molecular size of biomolecule-polymer conjugate has shorter blood plasma circulating time but increased bioactivity.

Unlike the conventional branched or linear polymer conjugates, the unique type Ia (n=2) or Ib (n=2) synergistic biomolecule-polymer conjugates integrate dual biological activities provided by large and small fragmented biomolecule-polymer conjugates and thus, providing combined increased biological activity in vivo. In addition, the biological activity in plasma may be sustained due to the gradually increase of biological activity from the small size biomolecule-polymer conjugates released from the large size synergistic conjugates.

The large molecular size of synergistic biomolecule-polymer conjugates provides better PK properties, including drug absorption, distribution, volume of distribution (Vd) and plasma half life. The small molecular size of the degraded biomolecule-polymer or the biomolecule-spacer conjugates from synergistic biomolecule-polymer has higher biological activity for achieving better pharmacodynamic properties. Thus, the synergistic biomolecule-polymer integrates the advantages of multiple (n>2) or dual (n=2) conjugates performance of large size of biomolecule-polymer and small size of biomolecule-polymer conjugates in vivo to provide combined enhanced biological activity and synergistically improved pharmacokinetic and pharmacodynamic properties of bioconjugate.

For n>2 or x>2, the synergistic biomolecule-polymer integrates the advantages of multiple conjugates effects of large size of biomolecule-polymer and small size of biomolecule-polymer conjugates in vivo to provide combined increased biological activity and combined enhanced pharmacokinetic and pharmacodynamic properties. According to the present invention, the smaller PEG polymers derived from the present conjugates have longer plasma half-life compared to their native forms and further are more effective at their target sites since they offer less steric hindrance at the binding site. Additionally, the harmonized PK-PD relationship offered by the plasma concentrations of large size biomolecule-PEG conjugates and the smaller size biomolecule-PEG conjugates enhance the overall biological activity in vivo. Such flexibility is markedly superior to prior art polymers that were unsuitable for circulation in the blood stream.

If n=2, the synergistic conjugates attached with cleavable-linkages linear polymer (Type II) is represented by the Formula IV:

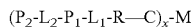

$(P_2$-$L_2$-$P_1$-$L_1$-R—C$)_x$-M wherein $P_1$ and $P_2$ may be the same or different polymer types and sizes; wherein $L_1$ linkage can be permanent or cleavable linkage; wherein $L_2$ linkage is cleavable. A cleavable spacer may be implanted between P1 and P2. The cleavable spacer compound comprises a releasable linkage L as described in Formulas I and II.

For Type IIa synergistic conjugates attached with permanent-cleavable-linkages branched polymers, wherein $L_1$ is a permanent linkage; wherein $L_2$ is a cleavable linkage.

If x=1, the Type IIa synergistic conjugates is gradually converted to $P_1$-$L_1$-R—C-M and $P_2$ in vivo via enzymes controlled mechanism. This unique synergistic biomolecule-polymer provides dual active biomolecule-polymer conjugates in vivo, including the large size synergistic biomolecule-polymer and the small fragmented biomolecule-polymer conjugates.

For Type IIb synergistic conjugates attached with all-cleavable-linkages linear polymers, both $L_1$ and $L_2$ are the cleavable linkages.

If x=1, the Type IIb synergistic conjugates is gradually converted to R—C-M+$P_1$+$P_2$ in vivo via enzymes controlled reactions. This synergistic biomolecule-polymer provides combined biomolecule-polymer conjugates in vivo, including the large size synergistic biomolecule-polymer and the small biomolecule-spacer conjugates.

When x=1 and n=2, the synergistic biomolecule-polymer conjugates with permanent-cleavable-linkages branched or linear polymers (Types Ia or IIa) in in vivo and/or blood plasma are degraded to $P_2$ and $P_1$-$L_1$-R—C-M fragments in the Formula I and Formula II. The synergistic conjugate in vivo is a hybrid biological active conjugates include both a large size synergistic conjugate and a released smaller size biomolecule-polymer conjugate, thus, providing a hybrid synergy activity and the synergistic enhanced PK and PD properties.

In the same manner when x=1 and n=2, the synergistic biomolecule-polymer conjugates with all-cleavable-linkages branched or linear polymers (Types Ib or IIb) in in vivo and/or blood plasma are degraded to $P_2$ and $P_1$ and R—C-M fragments in the Formula I and Formula II. The synergistic conjugate in vivo is a hybrid biological active conjugates include both a large size synergistic conjugate and a released smaller size biomolecule-spacer conjugate and thus providing a hybrid synergy activity and the synergistic enhanced pharmacokinetic and pharmacodynamic properties.

In contrast to the conventional branched polymer conjugates with permanent polymer linkages, the unique synergistic biomolecule-polymer conjugates (Types Ia, Ib, IIa, IIb) of the invention are the long-acting, synchronized continuous-release and hybrid synergy systems, which deliver the hybrid active biomolecules in vivo to provide drug synergism in a in vivo and/or plasma enzyme controlled fashion. Types Ia and IIa synergistic biomolecule-polymer conjugates are converted into smaller biomolecule-polymer fragments in plasma via enzymatic reactions. Types Ib and IIb synergistic biomolecule-polymer conjugates are converted to biologically active molecule containing a spacer molecule via enzymes controlled reactions. The novel synergistic biomolecule-polymer conjugates integrate the multiple effects generated from the in-vivo hybrid biomolecule-polymer conjugates and thus, providing enhanced combined biological activity and synergy PK and PD properties.

In at least one embodiment, the synergistic biomolecule-polymer conjugate of the invention provides cleavable linkages to reduce the size of biomolecule-polymer by releasing bulky polymers in vivo and thus, reducing the toxicity. The synergistic biomolecule-polymer conjugate provides therapeutic advantages over conventional protein-polymer for potential prophylactic treatments, such as factors VII, VIIa, VIII and IX for hemophilia, interferon-β for multiple sclerosis, glucocerebrosidase for Gaucher's disease and other genetic disorders.

In another aspect of the present invention, the synergistic biomolecule-polymer conjugates can be administered by a number of routes, such as parenteral, nasal, rectal, oral, or topical. The parental administration refers to subcutaneous, intravenous, intramuscular, intraperitoneal, intradermal injections or any other suitable infusion techniques.

In a more preferred embodiment of the present invention, the cleavable-linkages polymer attached to the synergistic biomolecule-polymer conjugates has the following distinct characters:
1. The polymer contains at least one cleavable and one permanent linkage or all-cleavable linkages.
2. The sizes of attached polymeric moieties are either equivalent or nonequivalent.
3. The types of attached polymer moieties are the same or different. For example, the cleavable-linkages polymer containing PEG and PEI (polyethylene imine) moieties may be used for RNAi, siRNA or DNA delivery.

Formation of synergistic biomolecule-polymer conjugates, the invention provides the options of using the same or different types and sizes of the polymers for the cleavable-linkages polymers thereby providing significant advantages in choosing appropriate linkages, polymer types and polymer sizes for optimizing proteins conjugation.

For Pegylation, polyethylene glycol is the polymer used for conjugation. The Type I synergistic biomolecule-PEG conjugate with permanent-cleavable-linkages of branched two-arms PEG polymers is described as the following Formula V:

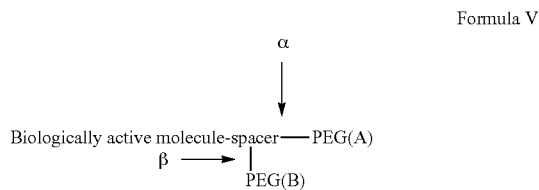

Formula V

Wherein PEG(A) and PEG(B) polymers may be of the same or different molecular weight.

For Type Ia synergistic biomolecule-PEG conjugates, α bond is a permanent linkage and β bond is a cleavable linkage. The Type Ia synergistic biomolecule-PEG is gradually converted to smaller biomolecule-spacer-PEG(A) conjugate in in vivo and/or plasma via enzymatic reaction.

For Type Ib synergistic biomolecule-PEG, α bond and β bond both are cleavable linkages in plasma. The linkages can be different types of releasable functional groups.

Unlike the conventional branched PEG linkers with symmetric arms, the present invention provides methods for the synthesis of either symmetric or asymmetric cleavable-branched and cleavable-permanent-branched PEG linkers. The synthetic methodology of the invention provides significant advantages in choosing a variety of linkages and different sizes of PEG polymers for synthesizing desired permanent-cleavable-PEG and all-cleavable-PEG polymers for protein conjugation. In addition, the same methodology can be applied for the synthesis of conventional branched polymers for desired polymers, linkage fragments and polymer sizes.

The cleavable-branched PEG polymer linker containing mixed-permanent-cleavable linkages is expressed as PEG (A, α; B, βB), which A and B represent the sizes of the PEG polymer and α and β are the types of linkage. For Example, Lys(α-10K mPEG, carbamate; 20K mPEG, Ester) Succinimidyl Suberate (Compound 5) is a permanent-releasable-linkages branched 30 KDa polymer contains carbamate and ester linkages connected with 10 KDa and 20 KDa PEG polymers, respectively. PEG Compound 10 Aspartic (carbamate; ester) and Compound 11, Glutamic (carbamate; ester) also are the mixed-permanent-cleavable linkages branched PEG polymer.

Type II synergistic biomolecule-PEG is the biomolecule attached with a linear but cleavable PEG linkages. The number of PEG polymers attached to biomolecules can varies from one single polymer strand to multiple polymer strands. The formula of Type II synergistic biomolecule-PEG connected with a linear PEG strand containing two pieces of PEG polymers is shown as follows:

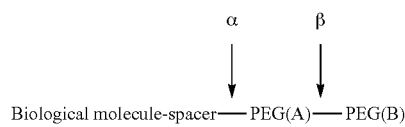

Wherein PEG(A) and PEG(B) may be of the same or different molecular weight. A spacer or a base molecule is implanted between biomolecule and PEG(A).

For Type IIa synergistic biomolecule-PEG, α bond is a permanent linkage and β bond is a cleavable linkage. A cleavable spacer may be implanted between PEG(A) and PEG(B). The cleavable spacer compound comprises a releasable linkage L as described in Formulas I and II The Type IIa synergistic biomolecule-PEG is gradually converted to smaller biomolecule-spacer-PEG(A) conjugate in plasma via enzymatic reaction.

For Type IIb synergistic biomolecule-PEG, α bond and β bond both are cleavable linkages. The linkages can be different types of cleavable linkages.

The mixed functional linkages on the PEG compound are marked with the symbols: α, β, γ, δ, etc.

For both Type Ib and Type IIb synergistic biomolecule-PEG, formation of biomolecule-spacer conjugate, both α and β bonds are cleavable in blood plasma. The spacer between biomolecule and PEG(A) can be designed for a specific use. It can be a drug, amino acid, peptide or an enhancer for permeating the blood brain barrier, or an enhancer improving biomolecule's efficacy.

PEG(A) or PEG(B) has a molecular weight between about 50 and about 40,000. A PEG polymer connected to the bioconjugate has molecular weight between about 100 and about 200,000. In a preferred embodiment the synergistic biomolecule-polymer conjugates, wherein P is PEG, the molecular weight of PEG (or mPEG) is in the range of is 5000, 10000, 12000, 20000, 30000, 40000 or mixed thereof.

One aspect of the invention is the R spacer is lysine connected to the permanent-cleavable-linkages two-arm branched methoxy poly(ethylene glycol) having structures represented by formulas VI and VII:

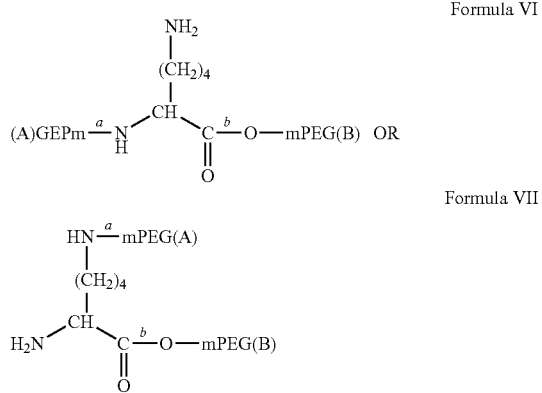

Wherein a bond designates a permanent linkage selected from the group consisting of amide, carbamate, carbamide, imide, amine, thiocarbamate, thiocarbamide, urethane and dithiocarbamate; wherein a bond is connected to either α or ε-amino group; wherein b bond is a cleavable linkage selected from the group consisting of carboxylic ester, carbonate, and carboxyl-imidazo; wherein the mixed linkages a and b are mixtures thereof; wherein mPEG(A) or mPEG(B) has a molecular weight from about 50 to 40,000; wherein the lysine mixed linkages di-substituted mPEG has a molecular weight from about 100 to 80,000.

For protein conjugation, the free amino of the lysine-mPEG(A)-mPEG(B) polymer further connects spacers comprising activated moieties selected from the group consisting of N-hydroxysuccinimide ester, p-nitrophenyl ester, N-succinimidyl carbonate, p-nitrophenyl carbonate, acylimidazo, aldehyde, maleimide, haloacetyl, carboxylic acid, hydroxyl, isocyanate, isothiocyanate, carbonyl, thiol, disulfide, amino, hydroxyl, hydrazide, and hydrazine.

In another embodiment, the a linkage is amine bond and the α- or ε-primary amino group is capable of undergoing reactions with second polymers containing electrophiles to form forked polymers, i.e. α or ε-amine connected with two polymer chains.

Compounds 5 and 7 both are the 30 KDa branched ester-carbamate-mixed-linkages PEG derivatives and the difference between them is the 10 k PEG permanent carbamate linkage position. The 10 k PEG carbamate linkage positions of compounds 5 and 7 are on the lysine-α and lysine-ε, respectively.

Compounds 6 and 8 both are the 30 KDa branched ester-amide-mixed-linkages PEG derivatives and the difference between them is the 10 k PEG permanent amide linkage position. The 10 k PEG amide linkage positions of compounds 6 and 8 are on the lysine-α and lysine-ε, respectively.

Compound 9 is the 30 KDa branched ester-carbamate-mixed-linkages PEG containing maleimido coupling group for protein sulfur (thio) moiety conjugation.

Compounds 10 and 11 are the type of branched ester-amide-mixed-linkages using aspartic and glutamic acids as the base chemicals for linking PEG polymers.

Various electrophilic and nucleophilic functional groups (C coupling groups in the formula) for protein conjugation can be synthesized, activated or inserted as the methods described in the examples.

The invention provides the methodology of synthesis of permanent-cleavable-linkages and all-cleavable-linkages polymer derivatives and asymmetric branched arms polymer for biomolecule conjugation. The synthetic methodology includes, but not limited to, the protection, de-protection, activation and insertion methods and procedures for the synthesis of permanent-cleavable-linkages or all-cleavable-linkages polymers.

The invention also provides a complete toolbox for choosing, optimizing and synthesizing a tailored permanent PEG size, a tailored releasable PEG size, a tailored permanent linkage, a tailored releasable linkage, tailored mixed PEG and polymer linkers and tailored different mixed polymers.

The invention also provides for a method of preparing synergistic biomolecule-polymer conjugate. For conjugation, the cleavable-linkages polymers are generally connected to a biomolecule having active sites selected from the group consisting of amino, thio, aldehyde, carboxyl and N-terminus.

In a preferred embodiment, the biomolecule of choice is an Interferon. As used herein, the term "interferon" refers to interferon-α, interferon-β, interferon-γ, interferon gamma-1b and interferon-λ (interferon lambda). Interferon-α includes Interferon-α-2a, Interferon-α-2b, Interferon-α-1, interferon alfacon-1 and consensus interferon. Interferons belong to the large class of glycoproteins known as cytokines and have therapeutic potential for a wide range of infectious and proliferative disorders. Interferons include Alpha interferon (IFN-α) which are proteins with biological effects such as antiviral, immunoregulatory, and antitumor activities. The recombinant IFN-α has been used as a therapeutic agent for the treatment of many diseases, including chronic hepatitis C, chronic hepatitis B, hairy-cell leukemia, non-Hodgkin's lymphoma, malignant melanoma, and chronic myelogenous leukemia.

At least one aspect of the present invention provides the permanent-cleavable-linkages branched PEG polymers for coupling interferons to produce synergistic interferon-PEG (Synergy-IFN-PEG) conjugates. The novel Synergy-IFN-PEG conjugates of the present invention are unique in vivo enzyme-controlled, continuous-release and hybrid synergy systems of interferon. The Synergy-IFN-PEG integrates the advantages of the larger molecule IFN-PEG conjugate and the released smaller molecule of IFN-PEG conjugate to provide combined increased interferon antiviral activity and enhanced pharmacokinetic and pharmacodynamic properties.

For Interferon-α, the unique synergistic Interferon-α-PEG (Synergy-IFN-α-polymer) conjugate of the invention is an advanced Interferon-α drug delivery technology that provides controlled, synchronized, continuous-release and hybrid synergy systems via enzyme reaction mechanism in vivo for delivering Interferon-α. The Synergy-IFN-α-polymer provides enhanced Interferon-α bioactivity and hybrid synergy pharmacological properties for achieving sustained absorption, enhanced antiviral activity, sustained antiviral activity, prolonged circulating half-life, reduced immunogenicity and toxicity, and enhanced potency. Furthermore, the sustained antiviral activity and enhanced PK and PD properties of the Synergy-IFN-α-polymer will have increased drug potency and clinically, may result in achieving greater sustained virological response, and subsequently reducing dose, dosing frequency, or the disease treatment period for hepatitis C patients.

The synergistic interferon-α-30 kPEG (α-10 k mPEG carbamate, 20 k mPEG ester) conjugate [Synergy-IFN-α-30 kPEG(α,β)] (Example 6) contains a cleavable 20 k mPEG ester linkage and a permanent 10 k mPEG carbamate linkage. The ester linkage of the conjugate is slowly hydrolyzed by in vivo plasma enzyme esterase to produce a smaller but more active α-Interferon-ε-amide-lysine-α-carbamate-10 kmPEG conjugate.

This unique enzyme controlled, continuous-release Synergy-IFN-α-30 kPEG(α,β) conjugate of the invention provides the in vivo increased antiviral effects from the enhanced combined activities of Synergy-IFN-α-30 kPEG(α,β) conjugate and the released IFN α-10 k PEG fragment. In the case of subcutaneous administration, the Synergy-IFN-α-30 kPEG (α,β) conjugate having larger molecular size has the advantage to be distributed with a smaller distribution volume and early on delivered on the liver and thus, it has longer plasma half-life. The IFN α-10 k PEG fragment slowly generated from the Synergy-IFN-α-30 kPEG(α,β) conjugate through enzymatic hydrolysis, however, has higher antiviral activity. The hybrid synergy system of Synergy-IFN-α-30 kPEG(α,β) provides synergistic effects for achieving an increased and sustained serum antiviral activity.

The number of permanent-cleavable PEG polymers attached to interferon can vary from one single (x=1) to multiple branched polymers (x>1). The synergistic interferon-PEG conjugate including Synergy-IFN-α-30 kPEG(α,β) in this invention can be interferon containing one single cleavable-linkages polymer or a mixture of interferon containing various numbers of cleavable-linkages polymers, preferably, x=1 to 2 or x=1 to 3.

The synergistic interferon-PEG conjugates of the invention, the preferred molecular weight of PEG (or mPEG) for the connected permanent-cleavable-linkages or all-cleavable-linkages branched PEG polymers is 5,000, 10,000, 12,000, 20,000, 30,000, 40,000 Da or mixed thereof. For the synergistic interferon-PEG conjugates, the preferred size of the attached PEG polymers is from about 10,000 to about 60,000 Da The synergistic biomolecule-polymer conjugates approach is particularly useful for cytokines, including interferons and interleukins.

Types Ia and IIa synergistic biomolecule-polymer conjugates may gradually release partial polymeric moieties to provide smaller size but more active biomolecule-polymer conjugate fragments in vivo. Types Ib and IIb synergistic biomolecule-polymer conjugates may gradually release all polymeric moieties to generate much more smaller but more active biomolecule-spacer conjugates in vivo. The amount of synergistic biomolecule-polymer conjugates (Types Ia. IIa, Ib or IIb) therefore gradually decrease in vivo and provide synchronized, continuous release of smaller size biomolecule-polymer or biomolecule-spacer conjugates via in vivo enzymes controlled mechanism. The hybrid biomolecule-polymer conjugates in vivo integrate multiple effects of the conjugates and thus, providing enhanced combined biological activity and synergistic PK and PD properties.

EXAMPLES

The following non-limiting examples illustrate certain aspects of the invention.

Example 1

Fmoc-Lys(Boc)-20K mPEG Ester 1

To a solution of 20 kDa mPEG (1 g, 0.05 mmol) and Fmoc-Lys(Boc)-OH (117 mg, 0.25 mmol) in anhydrous dichloromethane cooled in an ice-water bath was added dicyclohexylcarbodiimide (166 mg, 0.8 mmol), and the mixture was stirred under nitrogen and allowed to warm to room temperature overnight. The N,N'-dicyclohexylurea was removed from the reaction mixture by filtration. The filtrate was dried in vacuo. The residue was dissolved in anhydrous dichloromethane, and the white solid was precipitated by addition of tert-butyl methyl ether. The white solid product 1 was collected and washed with tert-butyl methyl ether.

Example 2

Fmoc-Lys(α-10K mPEG, Carbamate)-20K mPEG Ester 3

To a solution of Fmoc-Lys(Boc)-20K mPEG Ester 1 (0.8 g, 0.04 mmol) in anhydrous dichloromethane (4 mL) was added 4 mL of Trifluoroacetic acid. The reaction was stirred for one hour at room temperature, and the white solid was precipitated by tert-butyl methyl ether (70 mL). The solid product Fmoc-Lys-20K mPEG Ester 2 was collected and washed by tert-butyl methyl ether.

A solution Fmoc-Lys-20K mPEG Ester 2 (0.35 g, 0.018 mmol), 10K mPEG succinimidyl carbonate (SC-mPEG) (225 mg, 0.022 mmol), and triethylamine (110 mg, 1.08 mmol) in anhydrous methylene chloride (9 mL) was stirred at room temperature under nitrogen overnight. The reaction mixture was concentrated by partial removal of solvent under vacuum. The product Fmoc-Lys(α-10K mPEG, carbamate)-20K mPEG Ester 3 was precipitated by addition of tert-butyl methyl ether, filtered and collected. Product 3 can be further purified by chromatography.

Example 3

30 k Da Lys (α-10 kPEG Carbamate, 20 kPEG Ester) Succinimidyl Suberate Ester 5

Fmoc-Lys(α-10K mPEG, carbamate)-20K mPEG Ester 3 (0.5 g, 0.016 mmol) was dissolved in 11 mL of a mixture of dichloromethane/diethylamine (5:6), and the reaction mixture was stirred at room temperature for 3.5 hours. The solid product 4 was precipitated by addition of tert-butyl methyl ether (70 mL), filtered, and collected.

A solution of Lys(α-10K mPEG, carbamate)-20K mPEG Ester 4 (0.4 g, 0.013 mmol), Suberic acid bis(N-hydroxysuccinimide ester) (26 mg, 0.07 mmol) and triethylamine (3 mg, 0.03 mmol) in a mixture of anhydrous methylene chloride (7 mL) and dimethylformamide (3 mL) was stirred at room temperature under nitrogen for 9 hours. The reaction mixture was concentrated by partial removal of solvent under vacuum, and the white solid was precipitated by addition of tert-butyl methyl ether. The solid product 5 was collected and washed by tert-butyl methyl ether.

Example 4

Lys(α-10K mPEG, Amide)-20K mPEG Ester Succinimidyl Suberate 6

In this example, the ester-α-amide-mixed-linkages branched PEG derivative 6 was synthesized in the manner described in Examples 1, 2 and 3 except that the 10 k Dalton SC-PEG was replaced with 10 k Dalton mPEG-SCM (mPEG succinimidyl carboxymethyl). mPEG-SCM: $CH_3O-(CH_2CH_2O)n-CH_2-CO_2$-N-hydroxy succinimidyl ester.

Example 5

Lys($\epsilon$-10K mPEG, Carbamate)-20 KmPEG Ester $\alpha$-Succinimidyl Suberate 7

In this example, the ester-$\epsilon$-carbamate-mixed-linkages branched PEG derivative 7 was synthesized in the manner described in Examples 1, 2 and 3 except that the deblock of Fmoc step was carried out before the deblock of t-Boc step.

Example 6

Lys($\epsilon$-10K mPEG, Amide)-20K mPEG Ester $\alpha$-Succinimidyl Suberate 8

In this example, the ester-$\epsilon$-amide-mixed-linkages branched PEG derivative 8 was synthesized in the manner described in Example 5 except that the 10 k Dalton SC-PEG was replaced with 10 k Dalton mPEG-SCM (mPEG succinimidyl carboxymethyl). mPEG-SCM: $CH_3O-(CH_2CH_2O)n-CH_2-CO_2$-N-hydroxy succinimidyl ester

Example 7

3-Maleimidopropionyl Lys($\alpha$-10K mPEG, Carbamate)-20K mPEG Ester 9

A solution Lys($\alpha$-10K mPEG, carbamate)-20K mPEG Ester 4 (0.3 g, 0.01 mmol), 3-maleimidopropionic acid N-hydroxy succinimide ester (18.6 mg, 0.07 mmol), and triethyl amine (7.1 mg, 0.07 mmol) in 7 mL solvent mixture of anhydrous methylene chloride/dimethyl formamide (5:2) was stirred under nitrogen at room temperature overnight. The reaction mixture was concentrated by partial removal of solvent under vacuum, and the white solid was precipitated by addition of tert-butyl methyl ether (80 mL). The solid product 9 was collected and washed by tert-butyl methyl ether.

The 30 kDa 3-Maleimidopropionyl Lys($\alpha$-10K mPEG, carbamate)-20K mPEG Ester can be used for coupling with sulfhydryl(thio)-containing biomolecules to produce synergistic biomolecule-PEG conjugate.

Example 8

Preparation of Synergistic Interferon $\alpha$-30 kPEG (10 k mPEG Carbamate, 20 k mPEG ester) conjugate The recombinant Interferon $\alpha$ (2.8 mg/mL) in 5 mL of 2 mM acetic acid was mixed with 2 mL of 350 mM phosphate buffer, pH 8. After equilibrium, 82 mg of Lys ($\alpha$-10 kPEG carbamate, 20 kPEG ester) succinimidyl suberate ester 5, the activated 30,000 dalton mixed-permanent-cleavable linkages branched PEG, was added in portions to the IFN-$\alpha$ solution and stirred at room temperature for 3 hours. The IFN-$\alpha$ reaction mixture containing mono, di, and tri PEG branched polymers (composition x=1 to 3) was concentrated using 30 k Dalton molecular weight cut-off membrane (Sartorius Stedium Vivaspin 20) and further purified by size exclusion or ionic chromatography to collect desired Synergistic Interferon $\alpha$-2b-30 kPEG conjugates. The collected synergistic Interferon $\alpha$-Mono30 kPEG conjugate was concentrated using 30 k Dalton molecular weight cut-off membrane (Sartorius Stedium Vivaspin 20) and verified with size exclusion chromatography and SDS-PAGE electrophoresis.

Experiments for degradation of the interferon-$\alpha$-2b-30 kPEG (10 k mPEG carbamate, 20 k mPEG ester) conjugate and the release of 10 k PEG-interferon were conducted in human plasma at 37° C. The synergistic interferon $\alpha$-30 kPEG (10 k mPEG carbamate, 20 k mPEG ester) conjugate containing permanent carbamate and releasable ester linkages was incubated in human plasma at 37° C. for various periods of time, ranging from 0.5 to 36 hours. An aliquot plasma sample was withdrawn and treated with acetonitrile or acetonitrile/methanol organic solvent, vortexed, centrifuged, and concentrated. The solution residue was then analyzed by size exclusion chromatography or on Bis-Tris 4-12% SDS-PAGE gel with silver or iodine stain to confirm the release of 10 k PEG-interferon-$\alpha$-2b.

Example 9

Biological Data

In this example, the in vitro antiviral activities of IFN $\alpha$-2b, IFN-12 kPEG*, and synergistic 30 kIFN $\alpha$-2b-PEG(10 k mPEG carbamate, 20 k mPEG ester) conjugate from Example 8 were determined in a CPE assay employing New Wish cells challenged with EMCV virus. This cytopathic effect assay measures interferon's inhibitory effect on virus induced cell lysis. The endpoint of the assay is the dilution of IFN that gives 50% protection of the virus-infected target cells. The quantity of interferon present is determined relative to a reference standard of interferon. The antiviral activity of synergistic 30K IFN $\alpha$-2b-PEG was approximately 12% of that of interferon $\alpha$-2b. The results are listed in Table 1.

TABLE 1

| Interferon | antiviral activity (IU/mg) | residual activity (%) |
| --- | --- | --- |
| Interferon $\alpha$-2b | $2 \times 10^8$ | 100 |
| IFN $\alpha$-2b-12kPEG* | $5.2 \times 10^7$ | 26 |
| Synergy-IFN $\alpha$-2b-PEG | $2.4 \times 10^7$ | 12 |

Example 10

Pharmacokinetic Parameters

In this example, the various pharmacokinetic data were generated after subcutaneous injection into BALB/C mice. The pharmacokinetic parameters were determined using an average value obtained from the blood of 4 mice receiving the same amount of interferon, with time points taken over 3 days. For IFN-$\alpha$-2b-12 kPEG* and Synergy-30 kIFN $\alpha$-2b-PEG, blood samples were drawn at 1, 6, 24, 48, and 72 h after injection. For IFN $\alpha$-2b, blood samples were taken at 1, 3, 6, and 24 h after injection. Subsequently, the PK parameters were assessed and derived from a plot of antiviral activity against time. The comparative pharmacokinetic parameters are listed in Table 2.

Antiviral Assay: CPE Assay Using an EMCV Virus and New Wish Cells-Based Assay

AUC: Area Under Curve

TABLE 2

| Interferon | $T_{1/2}$ (hr) | Cmax (U/mL) | AUC (U-h/mL) |
|---|---|---|---|
| Interferon α-2b | 0.7 | — | 50,580,016 |
| IFN α-2b-12kPEG* | 15 | 71,680,000 | 973,844,360 |
| Synergy-30kIFN α-2b-PEG | 50 | 35,840,000 | 2,556,371,416 |

*IFN α-2b-12kPEG was prepared according to the literature published in Advanced Drug Delivery Reviews 54 (2002) 547-570.

In the case of subcutaneously injection, the pharmacokinetic data demonstrate that Synergy-30 kIFN α-2b-PEG prepared with 30 k Dalton molecular weight mixed-permanent-cleavable linkages branched PEG polymer is much superior over native Interferon α-2b and IFN α-2b-12 kPEG attached with conventional PEG linker in mammals. The serum half-life of Synergy-30 kIFN α-2b-PEG is 71 and 3.3 fold unexpectedly longer than those of unmodified Interferon α-2b and IFN α-2b-12 kPEG, respectively. The hybrid synergistic effects of Synergy-30 kIFN α-2b-PEG results in an unexpectedly significant increase of plasma AUC by over 50 fold in comparison with unmodified Interferon α-2b. Even more unexpected, the Synergy-30 kIFN α-2b-PEG even has 2.6 fold unexpectedly larger AUC than IFN α-2b-12 kPEG.

The pharmacokinetic of Synergy-IFN-α-30 kPEG(α,β) conjugate of the present invention integrates the dual PK properties of large IFN-30 kPEG and small 10 k IFN-α-PEG conjugates and provides a very flat profile of serum antiviral activity against time. The pK data indicates increased, sustained and consistent levels of interferon activity in vivo that would provide continual antiviral protection. The sustained antiviral activity, longer serum half-life and greater AUC also indicates that Synergy-IFN-α-30 kPEG(α,β) conjugate is more potent and clinically, may result in achieving greater sustained virological response.

Clearly, the synergistic 30 kIFN α-2b-PEG(10 k mPEG carbamate, 20 k mPEG ester) conjugate has distinct advantages over the unmodified IFN α-2b and IFN α-2b-12 kPEG in mammals. The Synergy-IFN-α-30 kPEG(α,β) conjugate unexpectedly improves the overall pharmacokinetics and pharmacodymamic properties that may result in a reduced dose, dosing frequency, or the disease treatment period for hepatitis C.

BOC: tert.Butyloxycarbonyl

Fmoc: 9-Fluorenylmethyloxycarbonyl $mPEG_{20K}$: mPEG molecular weight 20K Dalton $mPEG_{10K}$: mPEG molecular weight 10K Dalton Compound 1

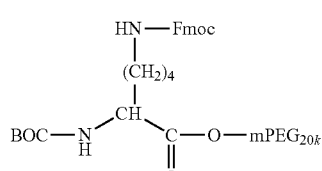

Fmoc-Lys(Boc)-20K mPEG Ester

Compound 2

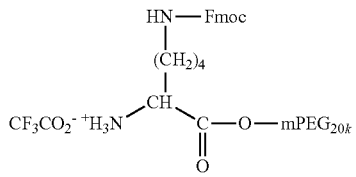

Fmoc-Lys-20K mPEG Ester

Compound 3

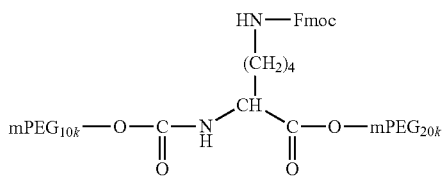

Fmoc-Lys(α-10K mPEG, carbamate)-20K mPEG Ester

Compound 4

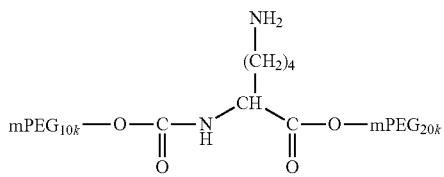

Lys(α-10K mPEG, carbamate)-20K mPEG Ester

Compound 5

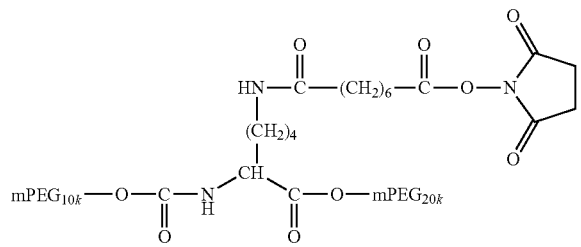

Lys(α-10K mPEG, carbamate)-20K mPEG Ester ε-Succinimidyl Suberate

Compound 6

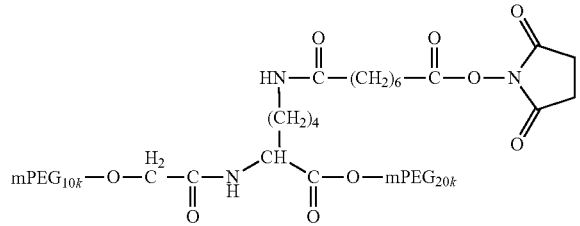

Lys(α-10K mPEG, Amide)-20K mPEG Ester ε-Succinimidyl Suberate

Compound 8

Lys(ε-10K mPEG, Amide)-20K mPEG Ester α-Succinimidyl Suberate

-continued

Compound 9

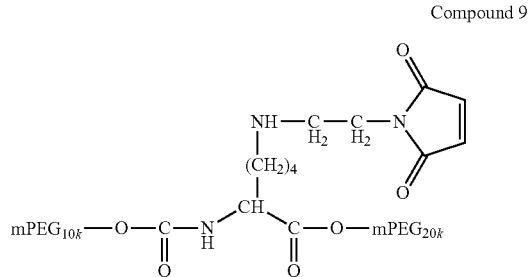

3-Maleimidopropionyl Lys(α-10K mPEG, carbamate)-20K mPEG Ester

Compound 10

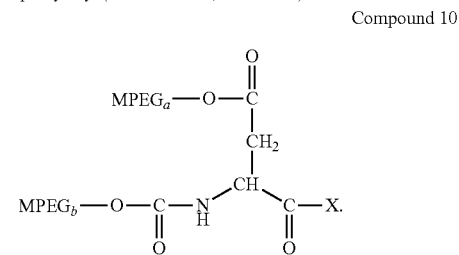

Aspartic (PEGa, ester; PEGb, carbamate), -C(O)X: activated ester, e.g. x = N-hydroxyscuccinide Compound 11

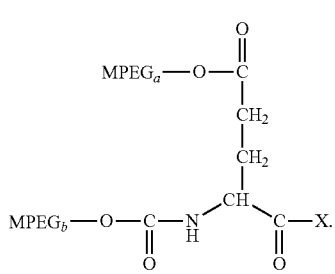

Glutamic (PEGa, ester; PEGb, carbamate), -C(O)X: activated ester, e.g. x = N-hydroxyscuccinide It should be emphasized that there are thousands of biomolecules, including proteins, macromolecules and small molecule therapeutic agents that can be effectively modified by attachment to the cleavable-linkages-polymer linkers of the invention. The synergistic biomolecule-polymer conjugates of the invention are the unique enzyme-controlled, continuous-release and hybrid synergy systems of biomolecules that may result in a number of potential clinical advantages over conventional pegylated biomolecule conjugates such as increased and sustained biological activity, enhanced PK and PD properties, prolonged circulating half-life, reduced toxicity and enhanced potency.

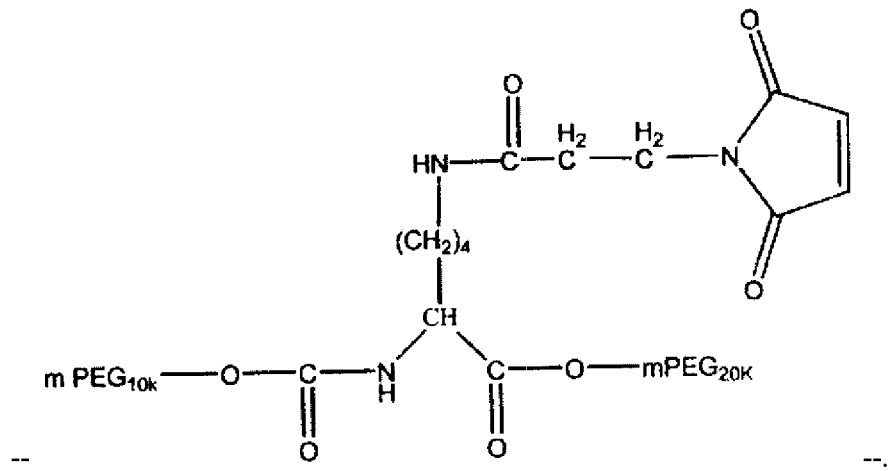

What is claimed is:

1. A synergistic biomolecule-polymer conjugate comprising the formula:

[(P-L)$_n$-R—C]$_x$-M wherein M is a biologically active biomolecule; wherein x is the number of cleavable-linkage polymers coupled to said biomolecule and x≥1; wherein n≥2; wherein P is a polymer or polymer lipid; wherein P$_n$ are multiple polymeric arms or pieces wherein their types and sizes may be the same or different; wherein L$_n$ is a functional linkage moiety comprising at least one cleavable linkage and at least one permanent linkage; or L$_n$ are all cleavable linkages; wherein R is a non-cleavable spacer connected between polymer and the biomolecule; and C is a coupling group attached to the biomolecule, wherein said synergistic biomolecule-polymer conjugate is cleaved in human blood plasma so that biologically active cleavage products are released.

2. The synergistic biomolecule-polymer conjugate of claim 1, wherein the permanent linkage is selected from the group consisting of amide, carbamate, imide, amine, urea, ether, sulfide, thiourea, thiocarbamate, and dithiocarbamate; and the cleavable linkage is selected from the group consisting of carboxylic ester, carbonate, sulfonic ester, phosphoric ester, acylimidazo and carbamate-imidazo.

3. The synergistic biomolecule-polymer conjugate of claim 1, wherein said coupling group C is selected from the group consisting of active ester, mixed anhydride, alkyl aldehyde, aromatic aldehyde, maleimide, haloacetyl, carboxylic acid, isocyanate, isothiocyanate, carbonyl, thiol, disulfide, amino, hydroxyl, hydrazide, and hydrazine, wherein said active ester is selected from the group consisting of N-hydroxysuccinimide ester, p-nitrophenyl ester, N-succinimidyl carbonate, p-nitrophenyl carbonate, acylimidazo and trichlorophenylcarbonate.

4. The synergistic biomolecule-polymer conjugate of claim 1, wherein R is selected from the group consisting of lysine, serine, threonine, cysteine, tyrosine, histidine, arginine, glutamic acid, aspartic acid, homocysteine, homoserine and ornithine.

5. The synergistic biomolecule-polymer conjugate of claim 1, wherein n=2, providing a cleavable-branched polymer conjugate comprising the formula:

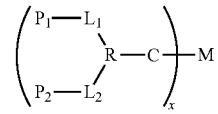

wherein L$_1$ is a permanent linkage and wherein L$_2$ is a cleavable linkage, providing a permanent-cleavable-linkage two-arm branched polymer; or wherein L$_1$ and L$_2$ both are cleavable linkages providing an all-cleavable-linkage two-arm branched polymer.

6. The synergistic biomolecule-polymer conjugate of claim 1, wherein P$_1$ and P$_2$ are methoxy poly(ethylene glycol); wherein R is lysine, having a structure represented by:

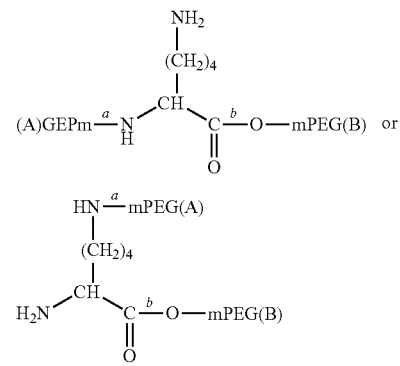

wherein bond a is a permanent linkage selected from the group consisting of amide, carbamate, urea, imide, amine, thiocarbamate, thiourea, and dithiocarbamate; wherein bond a is connected to either an α- or ε-amino group; wherein bond b is a cleavable linkage selected from the group consisting of carboxylic ester, carbonate, and carboxyl-imidazo, wherein the free amino group further connects spacers comprising activated moieties selected from the group consisting of N-hydroxysuccinimide ester, p-nitrophenyl ester, N-succinimidyl carbonate, p-nitrophenyl carbonate, acylimidazo, aldehyde, maleimide, haloacetyl, carboxylic acid, hydroxyl, isocyanate, isothiocyanate, carbonyl, thiol, disulfide, amino, hydroxyl, hydrazide, and hydrazine.

7. The synergistic biomolecule-polymer conjugate of claim 6, wherein the permanent-cleavable linkages branched PEG derivative includes Lys(α-10K mPEG, carbamate; 20K mPEG Ester) ε-Succinimidyl Suberate, Compound 5.

8. The synergistic biomolecule-polymer conjugate of claim 6, wherein the permanent-cleavable linkages branched PEG derivative includes Lys(α-10K mPEG, Amide; 20K mPEG, Ester) ε-Succinimidyl Suberate, Compound 6.

9. The synergistic biomolecule-polymer conjugate of claim 6, wherein the permanent-cleavable linkages branched PEG derivative includes Lys(ε-10K mPEG, carbamate; 20K mPEG, Ester) α-Succinimidyl Suberate, Compound 7.

10. The synergistic biomolecule-polymer conjugate of claim 6, wherein the permanent-cleavable linkages branched PEG derivative is Lys(ε-10K mPEG, amide; 20K mPEG, Ester) α-Succinimidyl Suberate, Compound 8.

11. The synergistic biomolecule-polymer conjugate of claim 6, wherein the permanent-cleavable linkages branched PEG derivative is 3-Maleimidopropionyl Lys(α-10K mPEG, carbamate)-20K mPEG Ester, Compound 9.

12. The synergistic biomolecule-polymer conjugate of claim 1, wherein M is an interferon selected from the group consisting of interferon-α, interferon-β, interferon-γ, interferon gamma-1b and interferon-λ (interferon lambda).

13. The synergistic biomolecule-polymer conjugate of claim 1, wherein M is an interferon-a selected from the group consisting of interferon-α-2a, interferon-α-2b, interferon-α-1, interferon alfacon-1 and consensus interferon.

14. A synergistic biomolecule-polymer conjugate of claim 1, wherein M is interferon-α-2b; wherein R is lysine, aspartic acid or glutamic acid; wherein $P_1$ and $P_2$ are mPEG and each one has a molecular weight ranging from about 50 to 40,000; wherein $L_1$ is an amide, carbamate or amine linkage and $L_2$ is a carboxylic ester or carbonate linkage.

15. A synergistic biomolecule-polymer conjugate of claim 1, wherein M is an interleukin or cytokine; wherein R is lysine, aspartic acid or glutamic acid; wherein $P_1$ and $P_2$ are mPEG and each one has a molecular weight ranging from about 50 to 40,000; wherein $L_1$ is an amide, carbamate or amine linkage and $L_2$ is a carboxylic ester or carbonate linkage.

16. A synergistic interferon α-30kPEG (10k mPEG carbamate, 20k mPEG ester) ε-Suberate conjugate comprising one single component, x=1, wherein the synergistic interferon conjugate is cleaved in human blood plasma so that biologically active cleavage products are released.

17. A synergistic interferon α-30kPEG (10k mPEG carbamate, 20k mPEG ester) ε-Suberate conjugate, wherein the conjugate comprises a mixture having composition x=1 to 2 or x=1 to 3, wherein the synergistic interferon conjugate is cleaved in human blood plasma so that biologically active cleavage products are released.

18. The synergistic interferon α-30kPEG (10k mPEG carbamate, 20k mPEG ester) conjugate of claim 16, wherein the interferon a is interferon α-2b.

19. A synergistic biomolecule-polymer conjugate of claim 1, wherein M is selected from the group of blood clotting factors consisting of clotting factors VII, VIIa, VIII and IX, and wherein the synergistic biomolecule-polymer conjugate is effective in prophylactic treatment for hemophilia.

20. The synergistic biomolecule-polymer conjugate of claim 1, wherein $P_1$ and $P_2$ are methoxy poly(ethylene glycol); wherein R is aspartic acid connected with said methoxy poly(ethylene glycol) having a structure represented by:

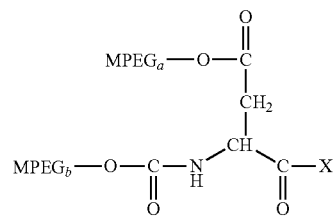

wherein the permanent linkage is selected from the group consisting of amide, carbamate, urea, imide, amine, thiocarbamate, thiourea, and dithiocarbamate; wherein the cleavable linkage is selected from the group consisting of carboxylic ester, carbonate, and carboxyl-imidazo; wherein X is an activated ester selected from the group consisting of N-hydroxysuccinimide ester, p-nitrophenyl ester, N-succinimidyl carbonate, p-nitrophenyl carbonate, and acylimidazo; or X is an aldehyde, maleimide, haloacetyl, carboxylic acid, hydroxyl, isocyanate, isothiocyanate, carbonyl, thiol, disulfide, amino, hydroxyl, hydrazide, or hydrazine group.

21. The synergistic biomolecule-polymer conjugate of claim 1, wherein $P_1$ and $P_2$ are methoxy poly(ethylene glycol); wherein R is glutamic acid connected with methoxy poly(ethylene glycol) having a structure represented by:

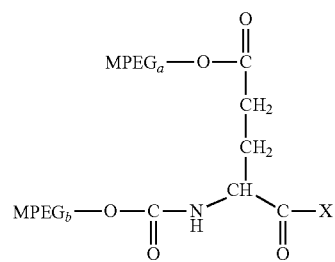

wherein the permanent linkage selected from the group consisting of amide, carbamate, urea, imide, amine, thiocarbamate, thiourea, and dithiocarbamate; wherein the cleavable linkage selected from the group consisting of carboxylic ester, carbonate, and carboxyl-imidazo; wherein X is an activated ester selected from the group consisting of N-hydroxysuccinimide ester, p-nitrophenyl ester, N-succinimidyl carbonate, p-nitrophenyl carbonate, and acylimidazo; or X is an aldehyde, maleimide, haloacetyl, carboxylic acid, hydroxyl, isocyanate, isothiocyanate, carbonyl, thiol, disulfide, amino, hydroxyl, hydrazide, or hydrazine group.

22. The synergistic biomolecule-polymer conjugate of claim 1, wherein the plasma cleavage provides controlled release of the biomolecule.

23. The synergistic biomolecule-polymer conjugate of claim 1, wherein the biologically active cleavage products are as active as, or more active than said synergistic biomolecule-polymer conjugate.

24. A method of treating hepatitis C, hepatitis B, hairy-cell leukemia, non-Hodgkin's lymphoma, malignant melanoma, or chronic myelogenous leukemia, comprising administering to a subject in need thereof an effective amount of the synergistic interferon α-30kPEG (10k mPEG carbamate, 20k mPEG ester) ε-Suberate conjugate of claim 16.

25. A method of treating hepatitis C, hepatitis B, hairy-cell leukemia, non-Hodgkin's lymphoma, malignant melanoma, or chronic myelogenous leukemia, comprising administering to a subject in need thereof an effective amount of the synergistic interferon α-30kPEG (10k mPEG carbamate, 20k mPEG ester) ε-Suberate conjugate of claim 17.

* * * * *

UNITED STATES PATENT AND TRADEMARK OFFICE
CERTIFICATE OF CORRECTION

PATENT NO. : 9,364,553 B2
APPLICATION NO. : 14/444555
DATED : June 14, 2016
INVENTOR(S) : Chyi Lee It is certified that error appears in the above-identified patent and that said Letters Patent is hereby corrected as shown below:

In the Specification:
At column 20, lines 55-65, please replace the structure of Compound 8:

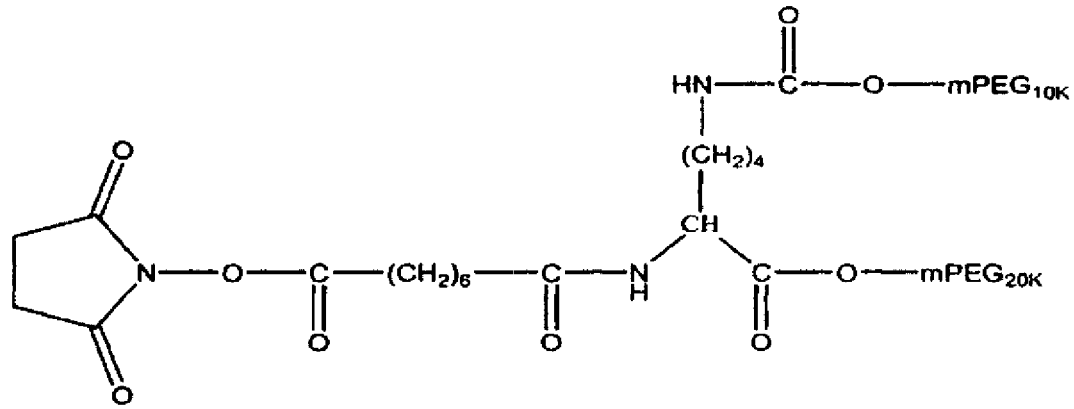

with the following:

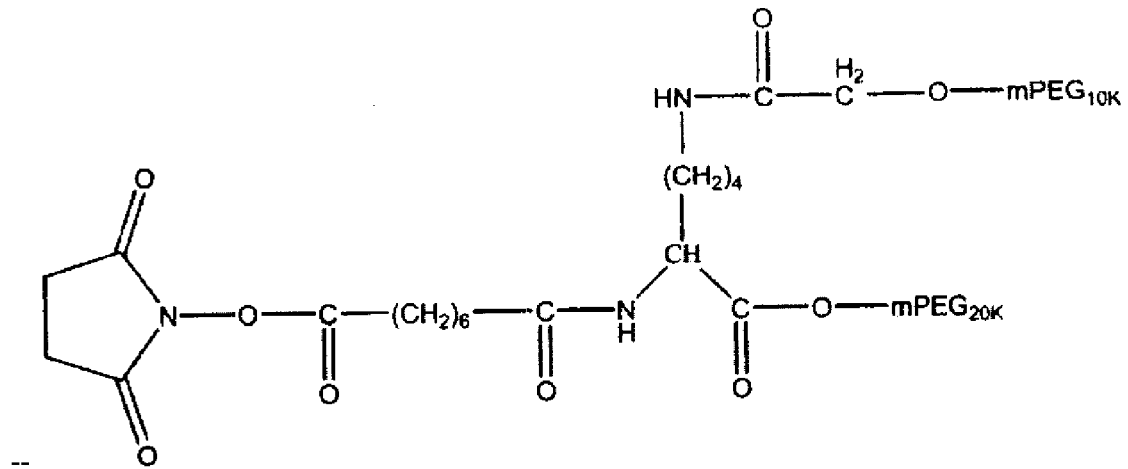

Signed and Sealed this
Sixteenth Day of August, 2016

Michelle K. Lee
*Director of the United States Patent and Trademark Office*

CERTIFICATE OF CORRECTION (continued)
U.S. Pat. No. 9,364,553 B2

At column 21, lines 5-10, please replace the structural formula of Compound 9:

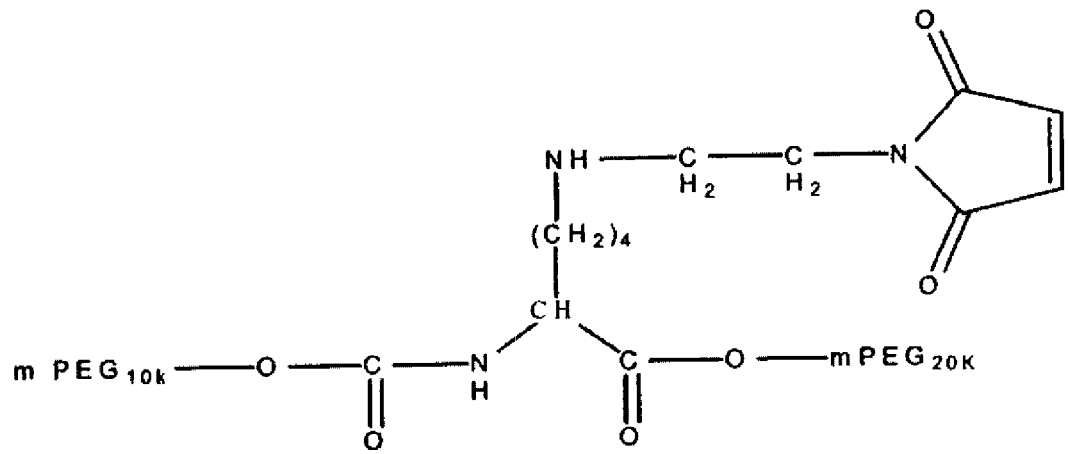

with the following: